United States Patent [19]

Lattin et al.

[11] Patent Number: 5,213,568
[45] Date of Patent: May 25, 1993

[54] ACTIVITY CONTROLLED ELECTROTRANSPORT DRUG DELIVERY DEVICE

[75] Inventors: Gary A. Lattin, Forest Lake; Rama Padmanabhan, Arden Hills; Michael J. Grace, Coon Rapids; Paul D. Sorenson, Blaine; Joseph B. Phipps, Plymouth; Larry A. McNichols, Coon Rapids, all of Minn.

[73] Assignee: Medtronic Inc., Minneapolis, Minn.

[21] Appl. No.: 671,267

[22] Filed: Mar. 18, 1991

Related U.S. Application Data

[63] Continuation-in-part of Ser. No. 502,422, Mar. 30, 1990, abandoned.

[51] Int. Cl.⁵ ............................................. A61N 1/30
[52] U.S. Cl. .................................................. 604/20
[58] Field of Search ............... 604/20, 21; 128/419 R, 128/803, 782

[56] References Cited

U.S. PATENT DOCUMENTS

| | | |
|---|---|---|
| 3,618,601 | 11/1971 | Richardson . |
| 4,109,645 | 8/1978 | Bachelli . |
| 4,141,359 | 2/1979 | Jacobsen et al. . |
| 4,146,029 | 3/1979 | Ellinwood, Jr. . |
| 4,292,968 | 10/1981 | Ellis . |
| 4,406,658 | 9/1983 | Lattin et al. . |
| 4,428,378 | 1/1984 | Anderson et al. . |
| 4,639,244 | 1/1987 | Rizk et al. . |
| 4,702,732 | 10/1987 | Powers et al. . |
| 4,704,119 | 11/1987 | Shaw et al. . |
| 4,725,263 | 2/1988 | McNicholas et al. . |
| 4,808,152 | 2/1989 | Sibalis . |
| 4,822,334 | 4/1989 | Tapper . |
| 4,942,883 | 7/1990 | Newman ..................... 604/20 X |

FOREIGN PATENT DOCUMENTS

| | | |
|---|---|---|
| 0191404 | 2/1986 | European Pat. Off. . |
| 0292930 | 11/1988 | European Pat. Off. . |
| 0299631 | 1/1989 | European Pat. Off. . |
| 0309093 | 3/1989 | European Pat. Off. . |
| 2562800 | 4/1984 | France . |
| 8607269 | 12/1986 | PCT Int'l Appl. ............. 128/419 R |
| 8808729 | 11/1988 | PCT Int'l Appl. . |

Primary Examiner—Lee S. Cohen
Attorney, Agent, or Firm—Merchant, Gould, Smith, Edell, Welter & Schmidt

[57] ABSTRACT

The electrotransport drug delivery device includes a patient activity sensor which is used to selectively deliver drugs based upon a measured physical activity of the patient.

14 Claims, 3 Drawing Sheets

ACTIVITY CONTROLLED ELECTROTRANSPORT DRUG DELIVERY DEVICE

This application is a continuation-in-part of application Ser. No. 07/502,422, filed Mar. 30, 1990, now abandoned.

BACKGROUND OF THE INVENTION

1. Field of the Invention

The present invention relates to transdermal electrotransport drug administration devices and, more particularly, to a patch system which includes a current generator and a patient activity sensor for feedback control of the rate of drug delivery.

2. Description of the Prior Art

Transdermal electrotransport is a method of applying a medication to a patient through the application of an electromotive force to drive chemicals through the skin. The electrotransport application of medicaments avoids many problems associated with the percutaneous delivery of drugs. Experimentation has been directed to, development of drugs suitable for electrotransport, and to patch electrode systems suitable for dispensing those drugs.

In general, there are two mechanisms for electrotransport. Iontophoresis generally refers to the transport of charged substances, while electrosmosis refers to the transdermal flux of a liquid solvent (e.g., the liquid solvent containing the uncharged drug or agent) which is induced by the presence of an electric field imposed across the skin by the donor electrode. As used herein the terms "iontophoresis" and "iontophoretic" refer broadly to either, the delivery of charged drugs or agents, the delivery of uncharged drugs or agents by the process of electrosmosis, or both.

The expressions "drug" and "therapeutic agent" are used interchangeably and are intended to have their broadest interpretation as any therapeutically active substance which is delivered to a living organism to produce a desired, usually beneficial, effect. In general, this includes therapeutic agents in all of the major therapeutic areas including, but not limited to, anti-infectives such as antibiotics and antiviral agents, analgesics and analgesic combinations, anesthetics, anorexics, antiarthritics, antiasthmatic agents, anticonvulsants, antidepressants, antidiabetic agents, antidiarrheals, antihistamines, antiinflammatory agents, antimigraine preparations, antimotion sickness preparations, antinauseants, antineoplastics, antiparkinsonism drugs, antipruritics, antipsychotics, antipyretics, antispasmodics, including gastrointestinal and urinary, anticholinergics, sympathomimetrics, xanthine derivatives, cardiovascular preparations including calcium channel blockers, beta-blockers, antiarrythmics, antihypertensives, diuretics, vasodilators, including general, coronary, peripheral and cerebral, central nervous system stimulants, cough and cold preparations, decongestants, diagnostics, hormones, hypnotics, immunosuppressives, muscle relaxants, parasympatholytics, parasympathomimetrics, proteins, peptides, psychostimulants, sedatives and tranquilizers.

The invention is also useful in the controlled delivery or peptides, polypeptides, proteins and other macromolecules. These macromolecular substances typically have a molecular weight of at least about 300 daltons, and more typically a molecular weight in the range of about 300 to 40,000 daltons. Specific examples of peptides and proteins in this size range include, without limitation, LHRH, LHRH analogs such as buserelin, gonadorelin, naphrelin and leuprolide, GHRH, insulin, heparin, calcitonin, endorphin, TRH, NT-36 (chemical name: N=[[(s)-4oxo-2-azetidinyl]carbonyl]-L-hystidyl-L-prolinamide), liprecin, pituitary hormones (e.g., HGH, HMG, HCG, desmopressin acetate, etc.), follicle luteoids, $\alpha$ANF, growth factor releasing factor (GFRF), $\beta$MSH, somatostatin, bradykinin, somatotropin, platelet-derived growth factor, asparaginase, bleomycin sulfate, chymopapain, cholecystokinin, chorionic gonadotropin, corticotropin (ACTH), erythropoietin, epoprostenol (platelet aggregation inhibitor), glucagon, hyaluronidase, interferon, interleukin-1, interleukin-2 menotropins (urofollitropin (FSH) and LH), oxytocin, streptokinase, tissue plasminogen activator, urokinase, vasopressin, ACTH analogs, ANP, ANP clearance inhibitors, angiotensin II antagonists, antidiuretic hormone agonists, antidiuretic hormone antagonists, bradykinin antagonists, CD4, ceredase, CSF's, enkephalins, FAB fragments, IgE peptide suppressors, IGF-1, neurotrophic factors, growth factors, parathyroid hormone and agonists, parathyroid hormone antagonists, prostaglandin antagonists, pentigetide, protein C, protein S, renin inhibitors, thymosin alpha-1, thrombolytics, TNF, vaccines, vasopressin antagonist analogs, alpha-1 antitrypsin (recombinant).

The prior art teach a variety of techniques suitable for controlling transdermal current generators. It should be understood that electrically assisted transdermal delivery of peptides and proteins as well as the phenomenon of electroosmosis, have been disclosed in the prior art. Examples of relevant art includes:

U.S. Pat. No. 3,618,601—teaches automatic control of an iontophoretic current source.

U.S. Pat. No. 4,808,152—teaches an adjustable iontophoretic generator with programmable output.

U.S. Pat. No. 4,141,359—teaches a feedback controlled current source with automatic shutdown in the presence of excessive voltage buildup U.S. Pat. No. 4,292,968—teaches a an iontophoretic generator which operates in a constant current mode, but which may operate in a constant voltage mode if in the presence of high electrode impedance.

PCT patent application WO 88/08729, teaches an iontophoretic drug delivery system which provides closed loop control of the driving current.

European patent application 0 309 093 EPA—teaches low frequency oscillator for the application of drugs. The device uses a waveform having rapid rise time and a slow fall off time.

U.S. Pat. No. 4,725,263—teaches a programmable constant current source for the transdermal application of drugs.

U.S. Pat. No. 4,406,658—teaches an iontophoretic device for the delivery of drugs. The circuitry includes a current control circuit which ramps the current values in accordance with a timer control circuit.

SUMMARY OF THE INVENTION

In contrast to this prior art, the present invention provides open loop feedback control of the rate of drug delivery as a function of a measurement of patient activity.

In particular, the present invention has particular utility in delivering drugs whose delivery rate is dependent upon the physical activity of a patient. Specific examples of such drugs and the corresponding patient motion or activity include the following: delivery of theophylline or epinephrine for the treatment of apnea; delivery of an antitussive such as dextromethorphan for the treatment of coughing; delivery of an anticonvulsant for the treatment of an epileptic seizure; delivery of insulin based upon the level of patient activity (e.g., lower insulin delivery rate for more vigorous levels of patient activity); delivery of antiparkinson agent in response to patient shaking; delivery of antispasmodics such as diazepam for treatment of muscle spasms; and delivery of an antiemetic such as scopolamine or meclizine, in response to motion, for the treatment of motion sickness.

This object and others will become apparent from the following detailed description when read in conjunction with the accompanying drawings.

BRIEF DESCRIPTION OF THE DRAWINGS

In the drawings, like reference numerals indicate corresponding structure throughout the several views in which.

DETAILED DESCRIPTION OF THE PREFERRED EMBODIMENT

In the following description, reference is made to an illustrative embodiment for carrying out the invention. It should be understood that other embodiments may be utilized without departing from the scope of the invention.

Some transdermally deliverable drugs should be administered at a rate which takes into account the underlying metabolic state or activity level of the recipient.

For example certain drugs are metabolized more rapidly during exercise. In these instances, the therapeutic dose of the drug rises with increases in exercise. By way of contrast, other drugs such as pain relieving drugs may be required in smaller doses during exercise because the recipient may be distracted by physical exercise and the mental concentration associated with the activity. In these instances, the therapeutic dose of the drug may be lower with increased exercise In general, charged drugs may be cationic or anionic in form. For these reasons the polarity of the electrode reservoirs must be adapted to the form of the drug.

Figure 1:
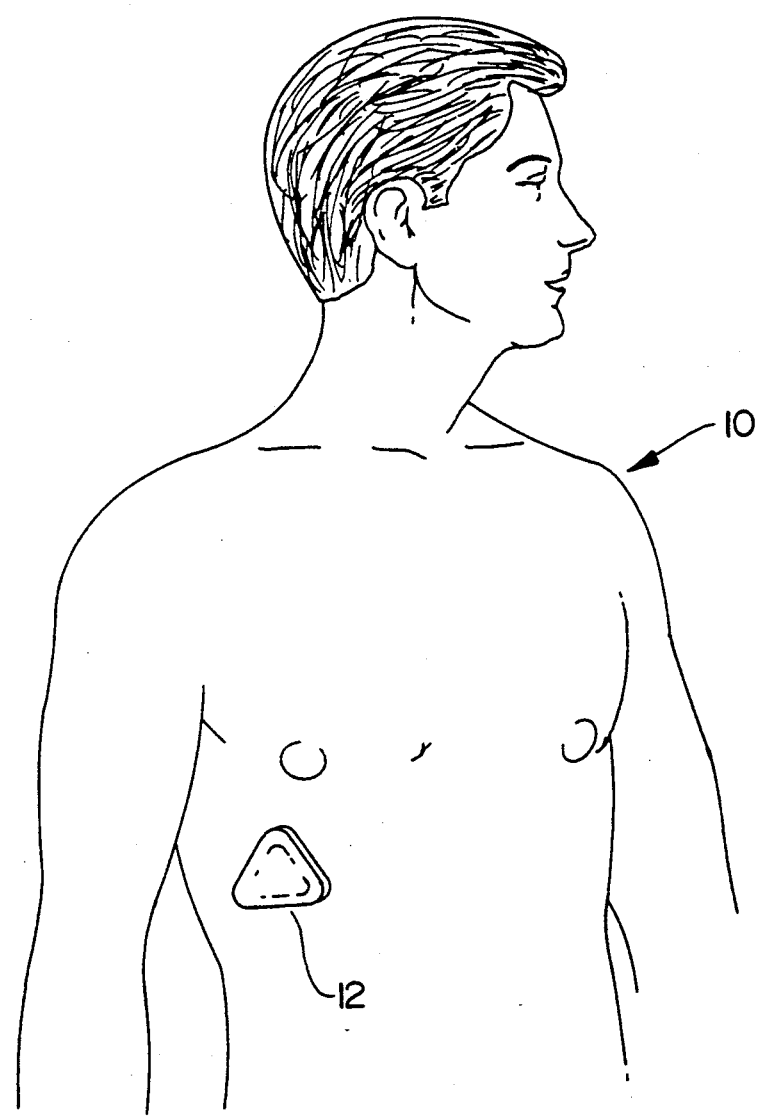
FIG. 1 depicts a patient using the iontophoretic delivery system.

FIG. 1 shows a patient 10 wearing the patch 12 on the chest. The iontophoretic transdermal drug delivery patch 12 includes drug reservoirs, a current generator, appropriate electrode areas and a suitable activity sensor.

The use of physical activity as a method of controlling a medical device is known from U.S. Pat. No. 4,428,378 issued Jan. 31, 1984 to Anderson, et al. This patent is incorporated by reference herein.

A variety of activity sensors may be used to access the patient's physical activity level. However, it is preferred to use a piezoelectric sensor of the type taught by the Anderson reference. It should be appreciated that other forms of activity sensing such as myoelectric sensing, may be used as well. In operation, the physical activity of the patient is detected by the sensor which is responsive to the body motion proximate the treatment site. In response to the physical activity of the patient, the current supplied to the patch electrode is regulated, which in turn controls the rate of drug administration. In many instances the rate of drug delivery should increase with increasing physical activity. However, in some instances the rate of drug delivery should decrease with increasing activity. The illustrative embodiment increases drug delivery with increases in activity.

Figure 2:
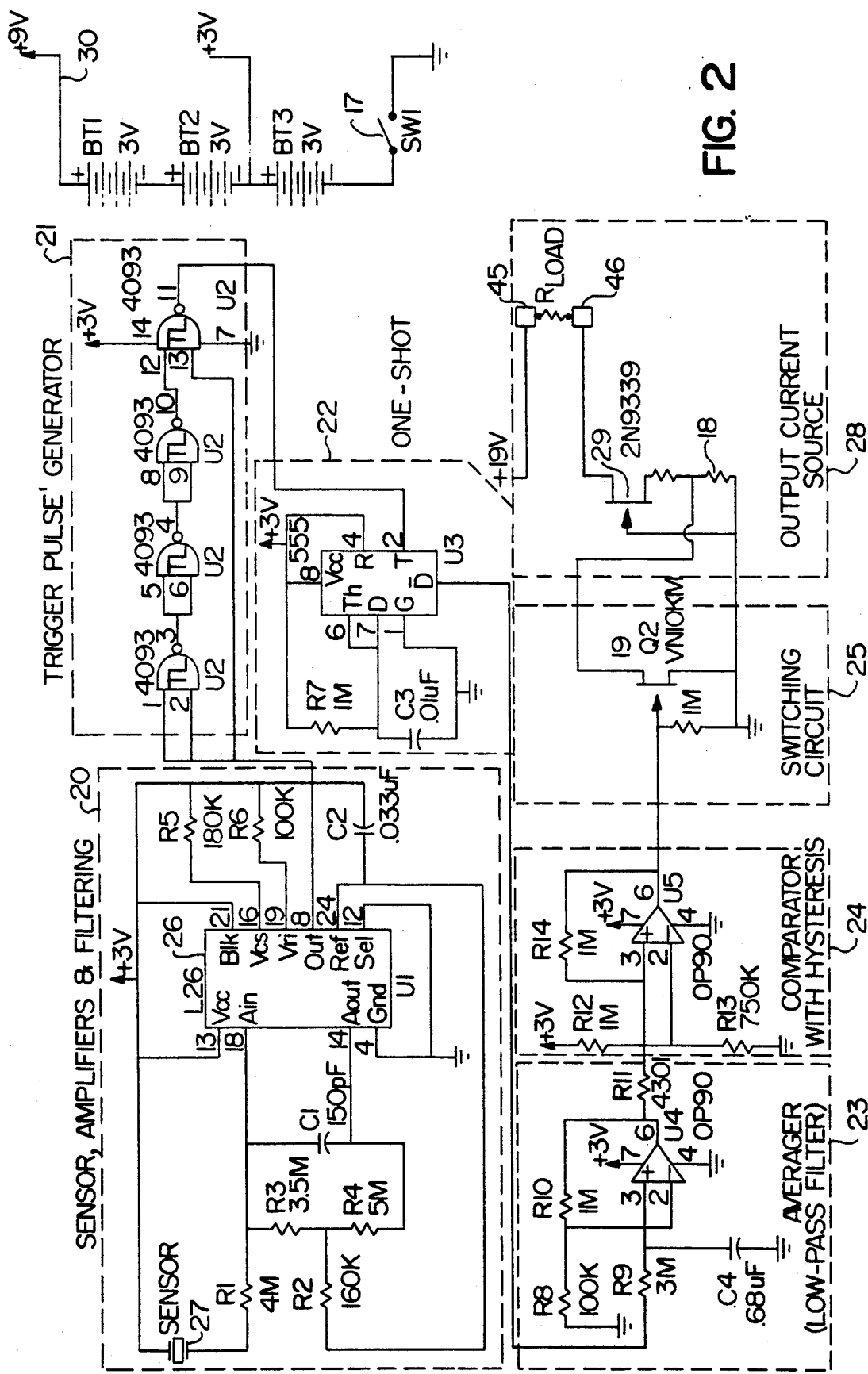
FIG. 2 is a functional block diagram showing the electronic portion of the invention.

FIG. 2 is a functional block diagram showing the electronic portion of the invention. The electronic portion of the invention is composed of several interconnected modules. An activity monitoring module 20 switches between a high and a low state with increasing frequency as activity increases. These level changes are applied to the trigger module 21. The trigger module contains a leading edge detector circuit to convert activity level changes to narrow trigger pulses. These trigger pulses trigger the one shot module 22 which in turn generates fixed pulse width pulses of approximately 10 ms. The output of the one shot module is low pass filtered by filter module 23. The output of the averager 23 is compared to a reference signal in comparator module 24. The switching module 25 switches the output current source 28 in response to the activity level of the patient.

The circuitry shown operates at a lower basal delivery rate and a higher activity based delivery rate.

In the absence of patient activity, the activity module generates essentially no activity counts. In this instance, the one shot module 22 output goes to a logic zero. After a brief delay related to the time constant of the averager module 23 the delivery rate drops to a minimum basal rate. In the presence of high patient activity the one shot operates at the activity based rate to establish a maximum drug delivery rate. The activity module 20, includes a piezo sensor 27 which is coupled to the patient. This type of transducer deflects in response to patient activity. This sensor is coupled to an integrated circuit 26 which incorporates certain circuit functions more fully described in the incorporated reference. However, in general the activity sensor tracks the activity motion signal of the body, and generates an output which is linearly proportional to the excitation frequency supplied to the sensor by the body. It has been found that this type of activity signal correlates well with the oxygen consumption of the patient over a wide range of activities. In operation the circuitry of module 20 generates activity counts which are supplied to trigger pulse generator 21.

The trigger pulse generator serves to buffer and square up the activity count pulses. It is preferred to use CMOS logic connected as a leading edge detector to perform this detection and trigger pulse stretching function The one shot module 22 receives the output of the trigger pulse generator. This trigger pulse generator 21 output signal is used as a triggering input to a triggerable one-shot multivibrator contained in one-shot module 22. The output of the one-shot is a fixed pulse width pulse. The output frequency of the one-shot module 22, tracks the triggering input frequency. In the absence of a trigger input the one-shot 22 output is at a logic zero state. As patient activity increases, pulses are supplied to an averager 23 at an increasing rate. The averager accumulates or integrates these pulses.

The function of the averager 23 is to prevent rapid excursions in the output current source 28 electrode drive circuit.

The comparator 24 compares the averaged output of the averager 23 with a reference value and toggles a switching circuit 25. Slight hysteresis is provided to ensure that rapid excursions of the current output do not take place.

The switching circuit 25 controls the output current source module 28. In operation, field effect transistor 29 operates in a constant current mode, sinking current from the 9 volt battery supply 30, through the reservoirs and electrodes. Field effect transistor 19 operates as a switch to shunt resistor 18 to increase the delivery rate to the higher activated determined value.

Figure 3:
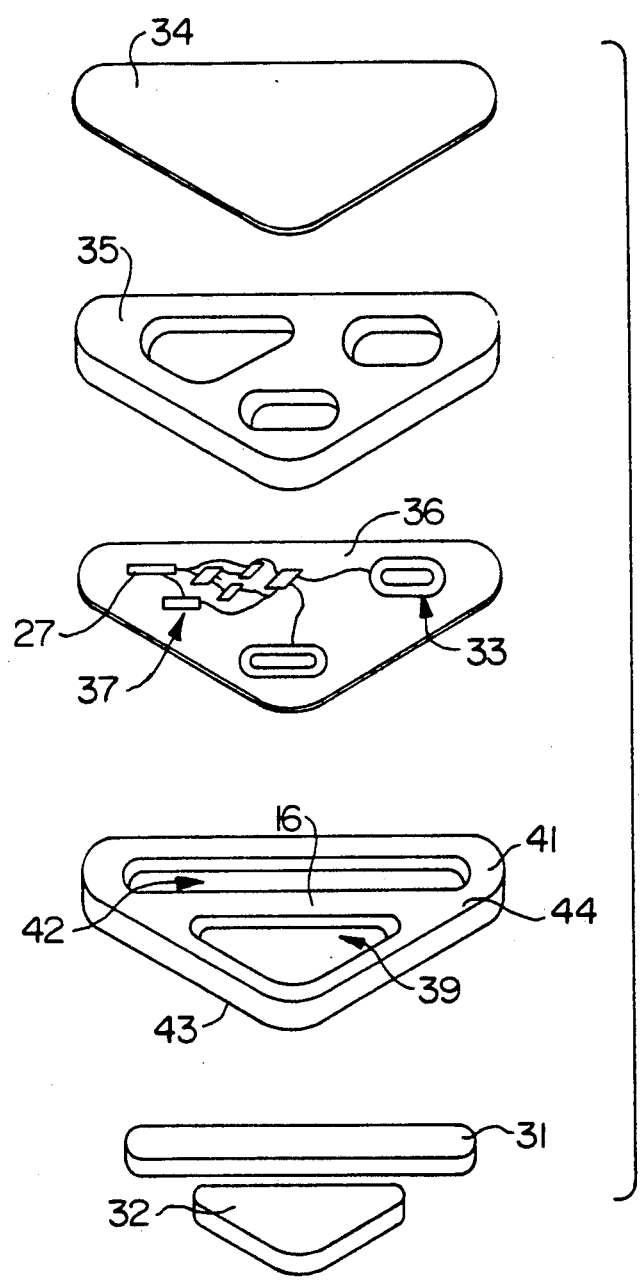
FIG. 3 is an exploded view of the iontophoretic patch depicting structural relationships between the elements of the device.

FIG. 3 is an exploded view of the iontophoretic "patch" depicting structural relationships between the elements of the device. It is preferred to dispense the patch as a unitary, disposable, single use drug delivery system. However it should be apparent that certain modifications may be made to the device described to render it reusable.

In general, an adhesive is used to mount the patch to the patient. This adhesive is attached to a conformal reservoir housing 41 on its under side 43. The separator 16 between the two reservoirs should have sufficient adhesive to isolate the two reservoirs 31, and 32 to prevent short circuiting of the patch. The upper surface 44 of the reservoir housing 41, may be adhesively attached to the flex circuit 36.

It is preferred to mount the various electronic components 37 on a flexible circuit board 36 to permit the patch to conform to patient contours. It is preferred to mount the activity sensor 38 on the flexible circuit board as well, to permit deflection of the circuit board to stress the piezo sensor. The deflection of the circuit board 36 communicates the patients physical motion to the sensor. A foam circuit housing 35 may be used to locate and protect the batteries 33 and other high profile circuit components. These electronic structures may be sealed by the use of a thin cover 34. The foam circuit housing 35 may be adhesively attached directly to the reservoir housing thus sealing the flex board within the patch.

A variety of drug delivery configurations are possible with the two reservoir patch.

In the preferred embodiment, a single gelled drug reservoir 32 is stored in a suitable cavity 39. In this configuration the drug reservoir 32 is connected to one of the circuit electrodes 45 or 46. In a similar fashion a salt may be gelled with a suitable material to form the a gelled counter- reservoir 31 skin connection. This other tissue connection is located proximate to the drug delivery reservoir to establish the current path of the circuit. As shown in the figure, the two reservoirs have different surface areas. It may be preferred to use the larger area reservoir 31 as the negative interface to reduce skin irritation.

In operation, either cavity 39 or 42 may contain the drug reservoir, depending upon whether the drug is in cationic or anionic form. It is conventional to store such drugs in solid phase gels, ointment gels or in a fiber matrixes. Additionally, it may be desirable to simultaneously dispense two separate drugs with one patch system. For example, a cationic drug may be placed in the first cavity while the second cavity may contain an anionic drug.

The activity sensor may switch the polarity in response to increased activity, thereby delivering a first cationic drug at a basal activity level and a second cationic drug in response to increased activity levels. Suitable switch reversal current sources are known from U.S. Pat. No. 4,406,658 which is incorporated by reference. This configuration may also be applied to two drugs in anionic form.

In use, the patch is activated by closing a suitable switch 17 which supplies current to the circuitry. The mounting adhesive on surface 43 may be exposed by removing a suitable wrapper. At this point the patch is placed on the skin of the patient. The patch may be used on the upper torso or other area where activity based measurements of patient activity are most accurately transcribed. This conformal structure provide adequate coupling between the patient and the sensor 27 to achieve this property.

What is claimed is:

1. Apparatus for the iontophoretic delivery of drugs to a patient comprising:
   a first reservoir containing a charged ionic substance for delivery to said patient;
   a first electrode coupled to said first reservoir;
   a second reservoir containing a charged ionic substance proximate said first reservoir;
   a second electrode coupled to said second reservoir;
   current generator means for supplying current to said first and second electrodes in response to a control signal;
   activity sensor means for monitoring the general level of physical activity of said patient and for generating an activity signal indicative of said general level of physical activity;
   control means coupled to said activity sensor means and to said current generator means, said control means responsive to said activity signal for generating a control signal for controlling said current generator means as a function of said activity signal.

2. The apparatus of claim 1 wherein said current generator means operates at a preset minimum current level in the presence of the general level of physical activity of said patient below a predetermined minimum.

3. The apparatus of claim 1 wherein said current generator means operates at a preset maximum current level in the presence of the general level of physical activity of said patient above a predetermined minimum.

4. Unitary iontophoretic drug delivery apparatus for transdermal delivery of a material to a patient's body comprising:
   a conformal carrier, including a reservoir means for storing gelled ionic substances;
   a flexible circuit package containing bodily motion monitoring circuitry and current delivery circuitry, coupled to said reservoir means for supplying current to said reservoir means;
   whereby the level of physical activity of said patient activates said bodily motion monitoring circuitry, controlling the delivery of said ionic substance as a function of the gross physical motion of said patient.

5. An iontophoretic drug delivery system for delivering two drugs to a patient comprising:
   a first cationic drug reservoir;
   a second anionic drug reservoir;
   current generator means coupled to said first and second reservoirs for supplying current to said reservoirs in response to a control signal;

activity sensor means for monitoring the general level of physical activity of said patient and for generating an activity signal indicative of said general level of physical activity;

control means coupled to said activity sensor means and to said current generator means, said control means responsive to said activity signal for generating a control signal for controlling said current generator means as a function of said activity signal.

6. An iontophoretic drug delivery system for delivering two drugs to a patient comprising:

a first cationic drug reservoir;

a second cationic drug reservoir;

current generator means coupled to said first and second reservoirs for supplying current to said first and second reservoirs in a first polarity in response to a first control signal and for supplying current to said first and second reservoirs in a second polarity in response to a second control signal;

activity sensor means for monitoring the general level of physical activity of said patient and for generating an activity signal indicative of said general level of physical activity;

control means coupled to said activity sensor means and to said current generator means, said control means responsive to said activity signal for generating a first control signal in the presence of low level of bodily motion and for generating a second control signal in the presence of higher level of bodily motion above a predetermined threshold.

7. An iontophoretic drug delivery system for delivering two drugs to a patient comprising:

a first anionic drug reservoir;

a second anionic drug reservoir;

current generator means coupled to said first and second reservoirs for supplying current to said reservoirs in a first polarity in response to a first control signal and for supplying current to said reservoirs in a second polarity in response to a second control signal;

activity sensor means for monitoring the general level of physical activity of said patient and for generating an activity signal indicative of said general level of physical activity;

control means coupled to said activity sensor means and to said current generator means responsive to said activity signal for generating a first control signal in the presence of low level physical activity and for generating a second control signal in the presence of higher level physical activity above a predetermined threshold.

8. Apparatus for the transdermal electrotransport of drugs to a patient comprising:

a first reservoir containing a charged ionic substance for delivery to said patient;

a second reservoir containing a charged ionic substance proximate said first reservoir;

current generator means coupled to said first and second reservoirs for supplying current to said first and second reservoirs in response to a control signal;

piezoelectric activity sensor means for monitoring the general level of physical activity of said patient and for generating an activity signal indicative of said general level of physical activity;

control means coupled to said piezoelectric activity sensor means and to said current generator means responsive to said activity signal for generating a control signal for controlling said current generator means as a function of said activity signal.

9. The apparatus of claim 8 wherein said current generator means operates at a preset minimum current level in the presence of patient physical activity below a predetermined minimum.

10. The apparatus of claim 8 wherein said current generator means operates at a preset maximum current level in the presence of patient physical activity above a predetermined minimum.

11. Unitary electrotransport drug delivery apparatus for transdermal delivery of a material to a patient's body comprising:

a conformal carrier, including a reservoir means for storing gelled ionic substances;

a flexible circuit package containing general level of physical activity monitoring circuitry adapted for application to said patient, and current delivery circuitry, coupled to said reservoir means for supplying current to said reservoir means;

whereby the general level of physical activity of said patient activates said general level of physical activity monitoring circuitry.

12. An electrotransport drug delivery system for delivering two drugs to a patient comprising:

a first cationic drug reservoir;

a second anionic drug reservoir;

current generator means coupled to said first and second reservoirs for supplying current to said reservoirs in response to a control signal;

piezoelectric activity sensor means for monitoring the general level of physical activity of said patient and for generating an activity signal indicative of said general level of physical activity;

control means coupled to said piezoelectric activity sensor means and to said current generator means responsive to said activity signal for generating a control signal for controlling said current generator means as a function of said activity signal.

13. An electrotransport drug delivery system for delivering two drugs to a patient comprising:

a first cationic drug reservoir;

a second cationic drug reservoir;

current generator means coupled to said first and second reservoirs for supplying current to said reservoirs in a first polarity in response to a first control signal and for supplying current to said reservoirs in a second polarity in response to a second control signal;

piezoelectric activity sensor means for monitoring the physical activity of said patient and for generating an activity signal indicative of said activity;

control means coupled to said piezoelectric activity sensor means and to said current generator means responsive to said activity signal for generating a first control signal in the presence of low activity and for generating a second control signal in the presence of higher activity above a predetermined threshold.

14. An electrotransport drug delivery system for delivering two drugs to a patient comprising:

a first anionic drug reservoir;

a second anionic drug reservoir;

current generator means coupled to said first and second reservoirs for supplying current to said reservoirs in a first polarity in response to a first control signal and for supplying current to said reservoirs in a second polarity in response to a second control signal;

piezoelectric activity sensor means for monitoring the physical activity of said patient and for generating an activity signal indicative of said activity;

control means coupled to said piezoelectric activity sensor means and to said current generator means responsive to said activity signal for generating a first control signal in the presence of low activity and for generating a second control signal in the presence of higher activity above a predetermined threshold.

* * * * *

UNITED STATES PATENT AND TRADEMARK OFFICE
CERTIFICATE OF CORRECTION

PATENT NO. : 5,213,568
DATED : May 25, 1993
INVENTOR(S) : Gary A. Lattin, et al

It is certified that error appears in the above-indentified patent and that said Letters Patent is hereby corrected as shown below:

On the cover page, Item [75] under Inventors:, after the name "Rama", please insert the initial --V.--

On the cover page, Item [63] under Related U.S. Application Data, after "1990,", please delete the word abandoned--

In column 1, line 6, after "Mar. 30, 1990,", please delete "now abandoned."

In column 1, line 23, after the word "to," and before the word "development", please insert the word --the--

In column 1, line 28, please delete the word "electrosmosis" and insert therefor --electro-osmosis--

In column 1, line 48, please delete the word "antiinflammatory" and insert therefor --anti-inflammatory--

UNITED STATES PATENT AND TRADEMARK OFFICE
CERTIFICATE OF CORRECTION

PATENT NO. : 5,213,568
DATED : May 25, 1993
INVENTOR(S) : Gary A. Lattin et al

It is certified that error appears in the above-indentified patent and that said Letters Patent is hereby corrected as shown below:

In column 2, line 32, please delete the word "electroosmosis" and insert therefor --electro-osmosis--

In column 2, line 41, after the word "teaches", please delete "a"

In column 3, line 47, after the word "exercise" and before the word "In", please insert --.--

In column 4, lines 53/54, after the word "function", please insert --.--

UNITED STATES PATENT AND TRADEMARK OFFICE
CERTIFICATE OF CORRECTION

PATENT NO. : 5,213,568
DATED : May 25, 1993
INVENTOR(S) : Gary A. Lattin, et al

It is certified that error appears in the above-indentified patent and that said Letters Patent is hereby corrected as shown below:

In column 5, line 48, after "to form the", please delete "a"

In column 5, line 59, after "gels or in" and before the word "fiber", please delete "a"

In column 6, line 12, after the word "structure", please delete the word "provide" and insert therefor --provides--

In column 6, line 14, please delete the word "property" and insert therefor --properly.--

Signed and Sealed this

First Day of March, 1994

Attest:

BRUCE LEHMAN

Attesting Officer

Commissioner of Patents and Trademarks